United States Patent
Yang et al.

(10) Patent No.: US 7,982,194 B2
(45) Date of Patent: Jul. 19, 2011

(54) SINGLE NANOPARTICLE TRACKING SPECTROSCOPIC MICROSCOPE

(75) Inventors: Haw Yang, Moraga, CA (US); Hu Cang, Berkeley, CA (US); Cangshan Xu, Berkeley, CA (US); Chung M. Wong, San Gabriel, CA (US)

(73) Assignee: The Regents of the University of California, Oakland, CA (US)

( * ) Notice: Subject to any disclaimer, the term of this patent is extended or adjusted under 35 U.S.C. 154(b) by 597 days.

(21) Appl. No.: 12/144,514

(22) Filed: Jun. 23, 2008

(65) Prior Publication Data
US 2011/0057121 A1    Mar. 10, 2011

Related U.S. Application Data

(63) Continuation of application No. PCT/US2006/062578, filed on Dec. 22, 2006.

(60) Provisional application No. 60/753,621, filed on Dec. 22, 2005.

(51) Int. Cl.
*H01J 37/244* (2006.01)
*H01J 37/20* (2006.01)
*G21K 5/10* (2006.01)

(52) U.S. Cl. ............ 250/492.1; 250/491.1; 250/397; 250/398; 356/496; 850/5; 850/30

(58) Field of Classification Search .......... 250/492.1, 250/491.1, 397, 398; 356/496; 850/5, 30
See application file for complete search history.

(56) References Cited

U.S. PATENT DOCUMENTS

| 5,337,140 A | 8/1994 | Hagiwara et al. |
| 5,576,831 A | 11/1996 | Nikoonahad et al. |
| 7,528,959 B2 * | 5/2009 | Novotny et al. ............ 356/496 |
| 2010/0207039 A1 * | 8/2010 | Ulcinas et al. ............ 250/492.1 |

OTHER PUBLICATIONS

Berg, Howard C. "How to Track Bacteria." The Review of Scientific Instruments 42(6): 868-871 (1971).
Cang et al. "Confocal three dimensional tracking of a single nanoparticle with concurrent spectroscopic readouts." Applied Physics Letters 88(223901): 1-4 (2006).
Cang et al. "Progress in single-molecule tracking spectroscopy." Chemical Physics Letters 457: 285-291 (2008).
Cohen. "Control of nanoparticles with arbitrary two-dimensional force fields." Physical Review Letters 94(118102): 1-4 (2005).
Enderlein. "Tracking of fluorescent molecules diffusing within membranes." Applied Physics B 71: 773-777 (2000).
Peters et al. "Three dimensional single-particle tracking with nanometer resolution." Review of Scientific Instruments 69(7): 2762-2766 (1998).
Sabanayagam et al. "High throughput scanning sonfocal microscope for single molecule analysis." Applied Physics Letters 84(7): 1216-1218 (2004).
International Search Report for Application No. PCT/US06/62578, "Single NanoParticle Tracking Spectroscopic Microscope" (2008).

* cited by examiner

*Primary Examiner* — Nikita Wells
(74) *Attorney, Agent, or Firm* — Robin C. Chiang; Lawrence Berkeley National Laboratory

(57) ABSTRACT

A system that can maintain and track the position of a single nanoparticle in three dimensions for a prolonged period has been disclosed. The system allows for continuously imaging the particle to observe any interactions it may have. The system also enables the acquisition of real-time sequential spectroscopic information from the particle. The apparatus holds great promise in performing single molecule spectroscopy and imaging on a non-stationary target.

22 Claims, 9 Drawing Sheets

SINGLE NANOPARTICLE TRACKING SPECTROSCOPIC MICROSCOPE

CROSS-REFERENCE TO RELATED APPLICATIONS

This application claims priority as a continuation application to PCT International Patent Application No. PCT/US2006/062578, filed Dec. 22, 2006, which claims priority to U.S. Provisional Patent Application Ser. No. 60/753,621, filed Dec. 22, 2005, both of which are hereby incorporated by reference.

STATEMENT OF GOVERNMENTAL SUPPORT

The invention described and claimed herein was made utilizing funds supplied by the U.S. Department of Energy under Contract No. DE-AC02-05CH11231. The U.S. government has certain rights in this invention.

TECHNICAL FIELD

This invention relates generally to a system for tracking a single particle and more specifically, to systems and methods for imaging and analyzing single particles.

BACKGROUND ART

Spectroscopic studies at the single-molecule or single-particle levels have provided invaluable information on the dynamics of complex systems in fields as different as materials science and molecular cell biology. These measurements eliminate the confounding ensemble average and provide direct observation of heterogeneity in space and time. To study long-term dynamics, a confocal or total internal reflection detection scheme has been used typically in conjunction with immobilized molecular or particle probes. This widely used experimental scheme, however, does not provide a direct correlation between local dynamics and the position of the molecule or particle in three dimensions, which can be a critical in understanding the link between microscopic processes and macroscopic phenomena.

There have been several proposed designs for following a particle in 3D non-invasively. In one example, an overfilled detector was used to detect the z position, and a position sensor was used to detect the x and y positions. The method relies on a lensing effect of a diffusive polystyrene sphere. A limit to the size of the bead is set by the diffraction limit of the light source and the difference in index of refraction between the bead and its surrounding medium. In another design, a target particle was excited with a rotating beam and the 3D position of the target was determined by off-line demodulating of the fluorescence signal. The resulting time resolution of 30-60 ms is dependent on the brightness of the particle and the integration time. Other methods that actively trap small particles or single molecules have also been demonstrated using, for instance, optical tweezers and two-dimensional electrical fields.

The program of a cell is encoded in the genes and executed by protein molecules. Genetic miscoding and aberrant folding of proteins, respectively, cause diseases such as sickle cell anemia and the neural degenerative Alzheimer's disease. Proteins in living cells exhibit motions that may be confined, directed, or diffusive. For example, with the use of fluorescent recovery after bleach (FRAP), the diffusion constant of green fluorescent proteins has been found to decrease from 87 $\mu m^2 s^{-1}$ in water to 25 $\mu m^2 s^{-1}$ in cytoplasm, to 20-30 $\mu m^2 s^{-1}$ in the mitochondrial matrix, and to 5-10 $\mu m^2 s^{-1}$ in the endoplasmic-reticulum lumen. These motions are often coupled to biochemical events involving the protein molecules that regulate cellular processes, such as sensing and response to stimulants and/or stress in the environment.

Single-molecule spectroscopy (SMS) is a uniquely powerful technique that affords close examination of the time trajectory and reactions of individual molecules that are otherwise hidden in the ensemble average. It is extremely difficult, if not impossible, using conventional spectroscopy, to observe the sequence of events in processes such as conformational dynamics of protein molecules and intermolecular interactions between enzymes and substrates. The dynamic configuration of biological macromolecules has direct implications on their time-dependent reactivity. Statistical analysis can be used to deduce dynamic configurations once the time dependence of the fluorescence intensity of biological labels is known. With SMS, in-depth understanding of the activities of individual biomolecules is possible, which is essential for the study of rare events that are hidden in the broad spatial-temporal distribution of a bulk experiment.

To date, most studies of single biological molecules have been conducted in vitro where the conditions are markedly different from those in a live cell or in a physiological system. Herein is disclosed apparatus and methods that make it possible to use SMS in a live-cell and in other complex environments.

DISCLOSURE OF INVENTION AND BEST MODE FOR CARRYING OUT THE INVENTION

In some embodiments of the invention, a system tracks a particle non-invasively and provides simultaneous particle position information. In other embodiments, single-molecule spectroscopy (SMS) is also performed on the particle. In other embodiments, the system tracks a nanoparticle while providing concurrent sequential position information and SMS measurements as the nanoparticle moves. In some arrangements, the movement, trajectory, and reaction pathways of single nanoparticles, fluorophores or molecules in diffusive, confined, or directed motions in complex systems, such as biological systems, can be quantified. Methods for using the systems are also disclosed.

Unlike active trapping approaches, the method disclosed herein is noninvasive and provides nanometer spatial resolution with sub-millisecond response time. In one arrangement, near-infrared (NIR) light scattered off a gold nanoparticle, to which a particle of interest can be tethered, provides a feedback signal that can be used for tracking. In other arrangements, fluorescence or photoluminescence from a single particle of interest can be tracked without using gold nanoparticles. An NIR light source has many advantages over a visible light source: photo-luminescence of the host material is reduced, depth of penetration is greater, especially when working with turbid samples, photo-damage of biological samples is minimized, and separation from the usual near-UV or visible excitation light used for SMS is easily achieved by spectral filtering.

In this disclosure, the term "particle" is meant to include small particles, nanoparticles, cells, and/or molecules that can move in a fluid and heretofore have been difficult to track for the purposes of microscopy and spectroscopy. In some arrangements, motions of the particles can be confined, directed or diffusive. In some arrangements, the particles can emit radiation. The term "light" is meant to include any or all electromagnetic radiation. The term "radiation" is meant to include any electromagnetic radiation or particle beam radiation. The term "beam" is used to mean a propagating stream of radiation, such as (charged) particles or electromagnetic energy. The term "beam splitter" is used to mean a device that splits a beam in two. For light, examples of devices that can split beams include glass prisms, half-silvered mirrors, and dichroic mirrored prisms. For particle radiation, examples of devices that can split beams include diffraction gratings and electron biprisms.

FIG. 1 is a schematic diagram of a system 100 for non-invasively tracking a particle, according to an embodiment of the invention. A particle 104 is coupled to a particle-holding device 108. The particle-holding device 108 has an x-y position control 112 and a z position control 116. In other arrangements the x control and the y control can be separate units. In some arrangements, the position controls 112, 116 are piezo-electric devices or stepper motors. Some other possibilities for position controls include dielectrophoresis, microfluidic flow, and magnetic force manipulation. The particle-holding device 108 can be any device that can contain the particle 104. Some examples of a particle-holding device include a mechanical microscope stage, such as one used commonly in confocal microscopy, an electric and/or magnetic field, and a fluid, perhaps within a microfluidic device.

There is a first radiation-gathering component 120 positioned to collect radiation 124 from the particle 104. The radiation beam 124 from the particle 104 can be any electromagnetic or particle radiation. In some arrangements, the radiation 124 is emitted from the particle in response to a stimulus, as for example, when a particle fluoresces after stimulation by light or by chemicals. In other arrangements, a radiation beam (not shown) is directed at the particle 104 and the beam 124 is scattered or refracted from the particle 104. In yet other arrangements, a radiation beam (not shown) is directed at the particle 104 and an interference signal is produced by the particle 104. An interference signal can arise when radiation waves (from the radiation beam directed at the particle 104) that interact with the particle 104 undergo a phase shift and then are rejoined with radiation waves that have not undergone a phase shift (e.g. from the original radiation beam). The first radiation-gathering component 120 is chosen to be appropriate for the type of radiation 124 collected from the particle 104. Examples of some pairings are shown in Table 1.

TABLE 1

| Radiation | Radiation-gathering component |
|---|---|
| microwave radiation | microwave lenses and mirrors |
| infrared radiation | infrared lenses and mirrors |
| ultraviolet radiation | uv lenses and mirrors |
| visible light | optical lenses and mirrors |
| x rays | x-ray lenses and mirrors |
| gamma rays | gamma ray lenses and mirrors |
| charged particles | electromagnetic lenses and mirrors |

Although the drawing in FIG. 1 shows the radiation 124 continuing straight through the radiation-gathering component 120, there are other possible radiation paths, depending on the component 120. For example, if a parabolic mirror is used as the radiation-gathering component 120, the radiation 124 path can be redirected back in a different direction.

The radiation-gathering component 120 directs the radiation 124 to a beam splitter 126 where the radiation is split along two different paths 130, 134. The beam splitter 126 is chosen to be appropriate for the type of radiation 124. In some arrangements where light radiation is collected, the beam splitter 126 is a half-silvered mirror. Other examples of beam splitters include crystals, acousto-optic or electro-optic devices, pellicle beam splitters, diffractive optics, or particle radiation beam splitters. The beam 130 may or may not have the same intensity as the beam 134. Although the figures shown herein show orthogonal radiation paths after radiation meets a beam splitter, the split radiation paths need not be at 90° to one another.

Along the beam path 130, a second radiation-gathering component 138 directs the radiation 130 through an aperture 142 and onto a radiation detector 146, such as a single-element radiation detector. In some arrangements, the second radiation-gathering component 138 focuses the radiation 130 just before or just after the plane of the aperture 142. The radiation detector 146 is of a type suitable for detecting the radiation 130. Examples of radiation detectors include avalanche photodiodes, photon-counting avalanche photodiodes, scintillators, photomultiplier tubes, charge coupled devices, Geiger counters, cameras, and matrix detectors. A first feedback control mechanism 152 provides communication from the detector 146 to the z control 116. The feedback control mechanism 152 provides information to the z control 116 about movement of the particle 104 in the z direction. The z control 116 moves the particle-holding device 108 to counteract the movement of the particle in the z direction so that the position of the particle in the z direction is stable. In some arrangements, the particle stability in the z direction is within ±100 nm. In some arrangements, the particle stability in the z direction is within ±50 nm. In some arrangements, the particle stability in the z direction is within ±15 nm. In some arrangements, the particle stability in the z direction is within ±5 nm.

Along the path 134, a third radiation-gathering component 156 directs the radiation 134 onto a position-sensitive radiation detector 160. The radiation detector 160 is of a type suitable for detecting the radiation 134. Examples of radiation detectors have been given above. A second feedback control mechanism 164 provides communication from the detector 160 to the x-y control 112. The feedback control mechanism 164 provides information to the x-y control 112 about movement of the particle 104 in the x direction and in the y direction so that the x-y control 112 can adjust the position of the particle 104 in the x direction and in the y direction as desired. The x-y control 112 moves the particle-holding device 108 to counteract the movement of the particle in the x-y plane so the position of the particle in the x-y plane is stable. In some arrangements, the particle stability in the x or y direction is within ±50 nm. In some arrangements, the particle stability in the x or y direction is within ±30 nm. In some arrangements, the particle stability in the x or y direction is within ±15 nm. In other arrangements, the particle stability in the x or y direction is within ±5 nm.

The feedback control mechanisms 152, 164 command the particle-holding device 108 to move by a distance δR, to counter the movement δr of the particle 104 as detected by the x-y position-sensitive radiation detector 160 and by the z position detector 146. Both δR and δr are vectors and can be of one, two, or three dimensions. The feedback control mechanism calculates δR from δr by using a feedback algorithm, such as a PID (proportional, integration and differentiation) algorithm. The feedback algorithm can be implemented by an analog circuit, a digital signal processor, a field-programmable-gate-array (FPGA), or software running on a computer or micro-controller.

There are many possible configurations for the position-sensitive radiation detector 160. In one embodiment of the invention, the position-sensitive radiation detector 160 is a quadrant detector. FIGS. 2A and 2B are schematic drawings that show another embodiment of the position-sensitive radiation detector 160. FIG. 2A shows a detector 160-2 as viewed along the incoming radiation beam 134. FIG. 2B shows a cross-section view of the detector 160-2 as cut along line B-B in FIG. 2A. The beam 134 strikes a mirror or prism 204 and is reflected into four orthogonal directions. The mirror or prism 204 is of a type that can redirect the kind of radiation in the radiation beam 134. The mirror or prism 204 can have any geometry that redirects the beam 134 into more than two directions. Examples include tetrahedral, square pyramidal and conical shapes. Redirected beams 212, 214, 216, 218 strike detectors 222, 224, 226, 228, respectively. For example, detectors 222, 226 can detect changes in beam intensities 212, 216, respectively, as the particle 104 moves in the ±x direction, and detectors 224, 228 can detect changes in beam intensities 214, 218, respectively, as the particle 104 moves in the ±y direction. Careful alignment of the incoming beam 134 with the mirror 204 and the detectors 222, 224, 226, 228 is useful. Information about changes in beam intensities are communicated to the x-y control 112 through the feedback control mechanism 164 and are correlated to movement of the particle 104, as described above.

FIGS. 3A, 3B, and 3C are schematic drawings that each show a portion of yet another embodiment of a position-sensitive radiation detector 160-3. In FIG. 3A, a second beam splitter 326 directs beam 134 along two separate beam paths 134x and 134y. There can be additional radiation-gathering components (not shown) in either or both of the beam paths 134x, 134y.

FIG. 3B shows x-movement detector 160-3x as viewed along the incoming radiation beam 134x. The beam 134x strikes a mirror or prism 303, that has the geometric shape of a triangular prism, and is reflected into two opposite directions. The mirror or prism 303 is of a type and shape that can redirect the kind of radiation in the radiation beam 134x. The mirror 303 can have any geometry that can redirect the beam 134x into two opposite directions. Redirected beams 312, 316 strike detectors 322, 326, respectively. The detectors 322, 326 can detect changes in beam intensities 312, 316, respectively, as the particle 104 moves in the ±x direction. Careful alignment of the incoming beam 134x with the mirror 303 and the detectors 322, 326 is useful. Information about changes in beam intensities 312, 316 are communicated to the x portion of the x-y control 112 through the feedback control mechanism 164 and are correlated to ±x movement of the particle 104. A cross section view through the long axis of FIG. 3B looks very much like the schematic shown in FIG. 2B.

FIG. 3C shows y-movement detector 160-3y as viewed along the incoming radiation beam 134y. The beam 134y strikes a mirror or prism 305, that has the geometric shape of a triangular prism, and is reflected into two opposite directions. The mirror 305 is of a type and shape that can redirect the kind of radiation in the radiation beam 134y. The mirror 305 can have any geometry that can reflect the beam 134y into two opposite directions. Redirected beams 314, 318 strike detectors 324, 328, respectively. The detectors 324, 328 can detect changes in beam intensities 314, 318, respectively, as the particle 104 moves in the ±y direction. Careful alignment of the incoming beam 134y with the mirror 305 and the detectors 324, 328 is useful. Information about changes in beam intensities 314, 318 are communicated to the y portion of the x-y control 112 through the feedback control mechanism 164 and are correlated to ±y movement of the particle 104. A cross section view through the long axis of FIG. 3C looks very much like the schematic shown in FIG. 2B.

FIG. 4 is a schematic diagram of a portion 400 of a system for non-invasively tracking a particle, according to an embodiment of the invention. Incident radiation 402 is directed at a particle 404 which is coupled to a particle-holding device 408. The incident radiation 402 can be any electromagnetic or particle radiation. Particle-holding device 408 is as described above for the particle-holding device 108 in FIG. 1. The incident radiation 402 impinges on the particle 404 and may stimulate the particle 404 to emit radiation 424 as in fluorescence (inelastic scattering). In other arrangements, radiation 424 from the particle 404 may be the result elastic scattering or refracting of the incident radiation 402. In yet other arrangements, the radiation 402 carries an interference signal after interacting with the particle 404. For ease of illustration, other components of the particle tracking system are not shown in FIG. 4.

FIG. 5 is a schematic drawing that shows an additional module 510 that can be added to a single particle tracking system 500, according to an embodiment of the invention. FIG. 5 includes many of the components that have been discussed in reference to FIG. 1. Incident radiation 502 is optional in the system shown in FIG. 5. The radiation-gathering component 120 collects radiation 124 from the particle 104, as has been discussed above. The additional module 510 includes a beam splitter 580 that directs a portion of beam 124 onto beam path 584 and directs the remainder of the beam 124 onto beam path 525. The beam 525 can continue on to be split by the beam splitter 126 and to provide feedback for x-y and z positioning as discussed above. For ease of illustration, the radiation detectors and x-y and z feedback controls have not been shown in FIG. 5. The radiation beam 584 is directed to a tool 588. In one arrangement, the tool 588 is an imaging system or microscope. In another arrangement, the tool 588 is a spectroscope. The spectroscope may contain its own light source and there can be addition components in the system to direct the spectroscope light onto the sample 104. This is discussed in more detail below. Other examples of tools 588 include interferometers and photon correlators. There can be any number of modules 510 containing any number of various tools 588 added to the particle tracking system 500.

Some particles or molecules can be difficult to track because they do not offer much contrast against background. To increase contrast and make tracking easier, a molecule of interest can be tethered to a metallic nanoparticle. Light scattered from the nanoparticle is collected by the tracking objective, and the intensity of the collected light is used in feedback loops (for the particle tracking system) to keep the particle in the focal volume. It is still possible to perform SMS on the tethered molecule as fluorescence photons can be collected by the SMS objective from which single molecule time trajectory and spectral properties can be acquired.

The use of a metallic nanoparticle as a tracer has several advantages. The small size of the nanoparticle, on the order of 40 nm or less, provides a non-obstructive biological label to cellular processes when attached to a biological macromolecule. Scattered light from a 60-nm gold particle may be equivalent to up to $3\times10^5$ times greater than the light emitted by a standard fluorescent dye, or by molecular fluoresce, depending on the wavelength used. A signal of this intensity is very useful in the particle tracking system. Furthermore, nanoparticles do not suffer from blinking or photobleaching, which can occur with fluorescent labels. Detected light from gold particles results from scattering, so it is possible to choose an illumination source, such as a laser in the near infrared region, that is biologically benign. The choice of an illumination source when using fluorescent labels is less flexible due to restrictions in excitation wavelengths. The wavelength of the tracking radiation can be chosen to avoid interference with SMS, if that is used in the system.

In one embodiment, the single particle tracking system is based on a confocal microscope and uses a near infrared laser and a dark-field condenser for illumination of a gold nanoparticle. Tracking is effected through fast feedback control of a 3-axis stage using dark-field optical signals from nanoparticles. In one arrangement, the stage is a piezoelectric stage. Laser-induced fluorescence of fluorophores attached to the nanoparticles can be measured using single-molecule spectroscopic (SMS) techniques. In one embodiment, by monitoring scattered light from the nanoparticle, the system brings a diffusive particle in a glycerol/water solution back to the focal volume of the microscope continuously with a spatial resolution of less than 210 nm and a response time of about a millisecond.

FIG. 6 is a schematic diagram that shows an exemplary system according to an embodiment of the invention. The system 600 is built around an inverted microscope. Near infrared (NIR) light from any number of 980 nm diode lasers 610 is combined by a fibercoupler and expanded to fill a 0.65-NA dark-field condenser 615 that focuses the NIR beam 613 at the sample 622. In one example, six lasers are used. In some arrangements, the intensity of the laser beam is adjusted between about 30 mW and 500 mW. The sample 622 is in a sample chamber 620 on a 3D piezo-electric translation stage 625 with a no-load resonance frequency of about 1.02 kHz at full swing. A 0.7-1.4 NA, 100× infinity-corrected oil immersion objective lens 630 is placed beneath the sample.

The scattered NIR light, collected by the objective lens, is split by a 50/50 beam splitter 635 to an x-y submodule 640 and a z submodule 645. The z submodule 645 has a 5-μm pinhole 650 placed slightly behind the conjugate focal point of a 0.85 NA, 60× objective lens 655. An aspheric lens 660 collects the light coming out of the pin hole 650 and focuses it onto an avalanche photo diode (APD) 665. Spatial resolution in the z direction arises from the intensity gradient created by throughput of light through the pinhole 650 as the target particle 622 moves in and out of focus. The z feedback control mechanism 695 locks in the initial signal intensity of the z APD 665 and attempts to maintain the same signal intensity by moving the z-axis on the piezo stage 625 or adjusting the focal plane.

The light going into the x-y submodule 640 forms an intermediate image by a 200-mm tube lens 670. A beam splitter 675 reflects part of the light to a video camera 680 for monitoring purposes. A 75-mm lens 685 is placed before a quadrant APD 690 of the x-y submodule 640. Using this two-stage setup, an overall magnification of approximately 750× is achieved for the x-y submodule. The x and y feedback mechanism maintains a null output of the quadrant APD 690 by continuously moving the nanoparticle 622 to the center of the laser beam 613 by adjusting the piezoelectric stage 625 in the x-y direction. In one arrangement, the feedback control mechanism has an analog design with a response time on the order of 5 ms.

A single molecule spectroscopy (SMS) system 605 is similar to the design used in standard confocal SMS configurations. Fluorescence signals as stimulated by excitation light and focused down to a diffraction-limited spot are collected from the focal volume and focused through a pinhole onto a sensitive photon detector such as an avalanche photodiode, after passing through an emission filter. The pinhole can suppress background so that emission from a single molecule is easier to observe. Because of the single particle tracking system, the target particle remains in focus even as it moves in three dimensions, thus making it possible to perform this kind of SMS investigation. For the spectroscopic probe, a 532-nm laser beam 618 from a solid-state laser (included within the SMS system 605 in FIG. 6) is coupled into the back aperture of the objective lens 630 through a long-pass dichroic mirror 632. The objective lens 630 focuses the light at the sample 622. A second, short-pass dichroic mirror 637 can separate the NIR tracking light 613 from the optical output of the green interrogation beam (i.e., the fluorescence signal from the sample 622. The optical output is focused by a 180-mm tube lens 640 in the microscope and detected by an APD 647.

In one embodiment, the various parts of the particle tracking system are operated using software that has three major components. The components can be run on one or on three separate computers. The software itself can be developed in C++ using the Microsoft Foundation Class Library (MFC) that provides all the tools to facilitate the development of a user-friendly graphical interface. Component 1 provides the user a real-time image from the CCD camera 680 while continuously monitoring the human interaction device (HID) for control of the piezoelectric xyz stage 625 and for engagement and disengagement of tracking. Upon engagement of tracking using the HID, Component 1 engages the system in a feedback control loop. Component 2 records live images of the sample in the field of view of the top objective continuously while a trigger pulse initiates Component 3 to record the time trajectory of a single molecule. The components are well-synchronized in order to avoid any time lapse in the sequence of events.

The system is capable of keeping a nanoparticle, which is moving in a medium equivalent to the medium of a living cell, within the focal volume of a diffraction-limited illumination area. This allows the activities of the attached biomolecule to be monitored continuously with state-of-art SMS. The movement of biomolecules and their respective biochemical activities can be thus correlated, opening up a range of exciting in vivo studies not currently possible.

Experimental Data

The spatial and temporal responses of the system were first characterized using immobilized 250-nm gold colloid particles spin-coated on a glass cover slip. A target particle was selected by using a video camera and a joystick to steer a particle into the focal region. Upon engaging the x-y feedback mechanism, the stage brought the target particle to the center of the focal region. Recordings of the x y and z stage movements as a function of time are shown in FIG. 7. The insets zoom in at the trajectories during the first several milliseconds, just before and after the feedback control mechanisms engage. As shown in FIG. 7, the response time is less than 500 μs for both the x and the y directions. As z positioning is also sensitive to fluctuations in x-y positioning, the z-feedback mechanism was engaged after the x-y positioning stabilized. Histograms of the fluctuations in the x, y and z directions are shown on the right side of FIG. 7, where the standard deviations have been determined to be 10 nm, 14 nm, and 34 nm, respectively. The fluctuations are caused mainly by mechanical and electronic noise.

The system was tested on a moving particle and demonstrated simultaneous single particle tracking and spectroscopic readouts. In this experiment, a second green laser was used to interrogate the tracked particle. The back-scattered light of the green beam was taken as the spectroscopic optical readout. The sample contained 250-nm gold particles diluted in a drop of a 3% (v/v) water in glycerol solution and was sandwiched between two cover slips. The edges of the cover slips were sealed with wax to prevent leakage. Particle movements were studied under non-equilibrium conditions. The sample was nudged to create a sheared flow and data was taken before the sample was able to re-equilibrate.

The intensity of the back scattered green light as measured by an APD and plotted as a function of time is shown in FIG. 8A. The arrow indicates the time when the tracking mechanism is engaged. With negligible laser noise, the variation in the green light intensity is due to fluctuations in the positioning of the particle. FIG. 8B shows a histogram of the green light intensity, with the abscissa normalized by the maximum photon count and the ordinate normalized by the total number of data points in the trajectory. The histogram exhibits a bell shape centered just below 0.5. The deviation of the maximum position from 1 corresponds to the difference, $\Delta$, between the green light focus point and the tracking origin, and the width indicates the standard deviations $\sigma_x$, $\sigma_y$, $\sigma_z$. In this experiment, the z position was not decoupled from the x-y position sensing, so the performance is somewhat degraded.

The 3D position of the particle was deduced from the stage movement through its built-in capacitive sensor and digitized every 333 μs. FIG. 9A shows the 3-dimensional trajectory of a 250-nm gold particle obtained by measuring the counter movement of the translation stage. For clarity, only one of every 10 points is shown. The non-equilibrium condition of the sample is indicated by the directional flow along the y direction. The dotted line in FIG. 9B is a plot of the mean square displacement of the gold particle from the origin as a function of time. The solid line is a fit to a mixed diffusive and directional particle motion.

In another embodiment of the invention, a method of tracking a particle is provided. First a particle or a molecule tethered to a particle is placed in a particle-holding device, such as a microscope stage. The device has at least an x-y position control and a z position control. Then a first radiation-gathering component, such as a lens, collects radiation from the particle. The particle radiation can occur as a result of fluorescence or some other excitation reaction, or it can be scattered or deflected by the particle from an incident radiation beam. The particle radiation is split along two distinct paths, a first path and a second path. The radiation along the first path is directed through an aperture and onto a single-element radiation detector, such as an APD. The single-element detector provides information to the z position control of the particle-holding device through a feedback mechanism. The radiation along the second path is directed onto a position-sensitive radiation detector. The position-sensitive detector provides information to the x-y position control of the particle-holding device through a feedback mechanism. The feedback mechanism interprets the information from the detectors and adjusts the position of the particle-holding device to maintain the position of the particle.

BRIEF DESCRIPTION OF THE DRAWINGS

The figures are for illustrative purposes only and are not drawn to scale.

INDUSTRIAL APPLICABILITY

Figure 1:
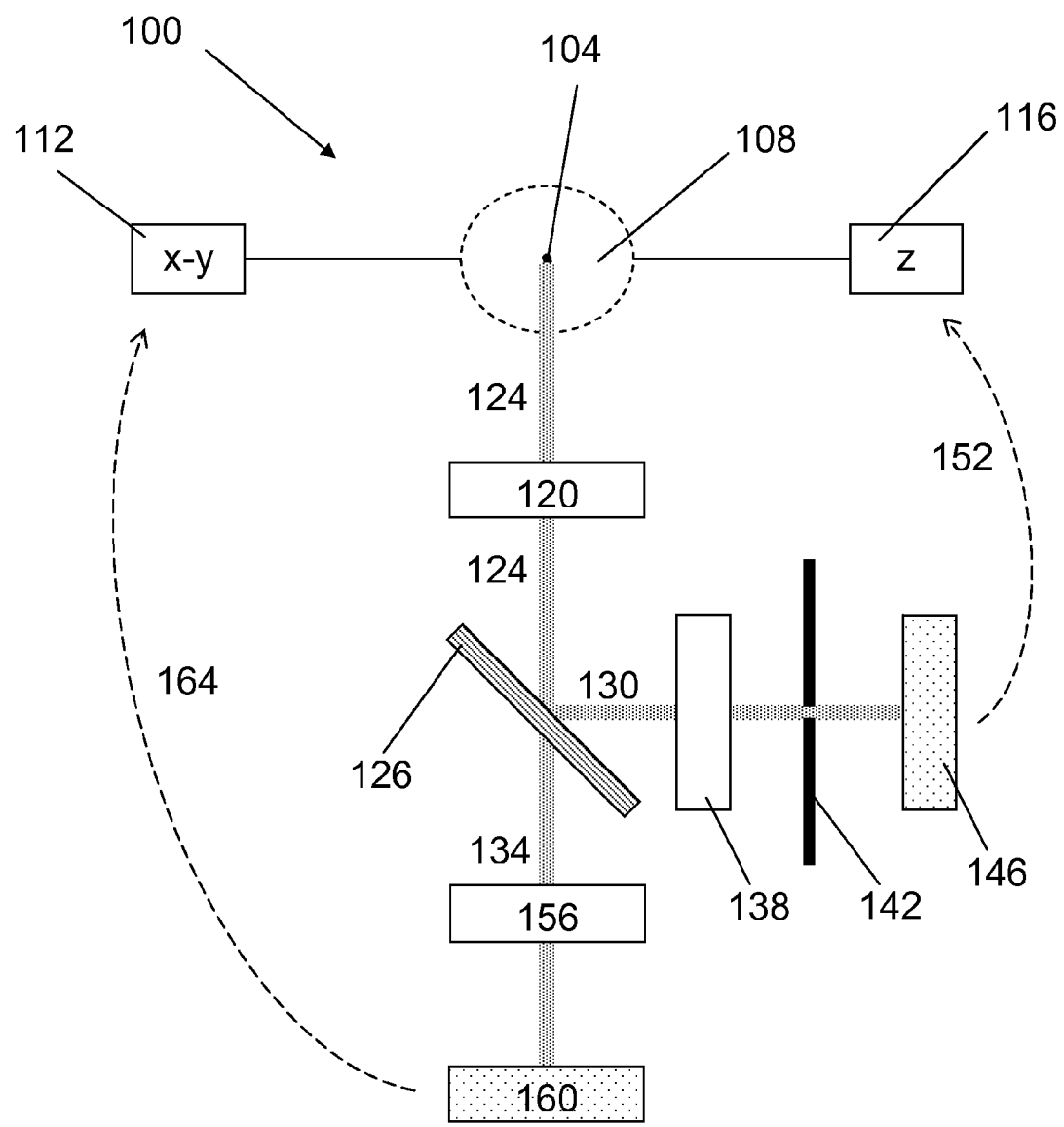
FIG. 1 is a schematic diagram of a system for non-invasively tracking a particle, according to an embodiment of the invention.
Figure 2A:
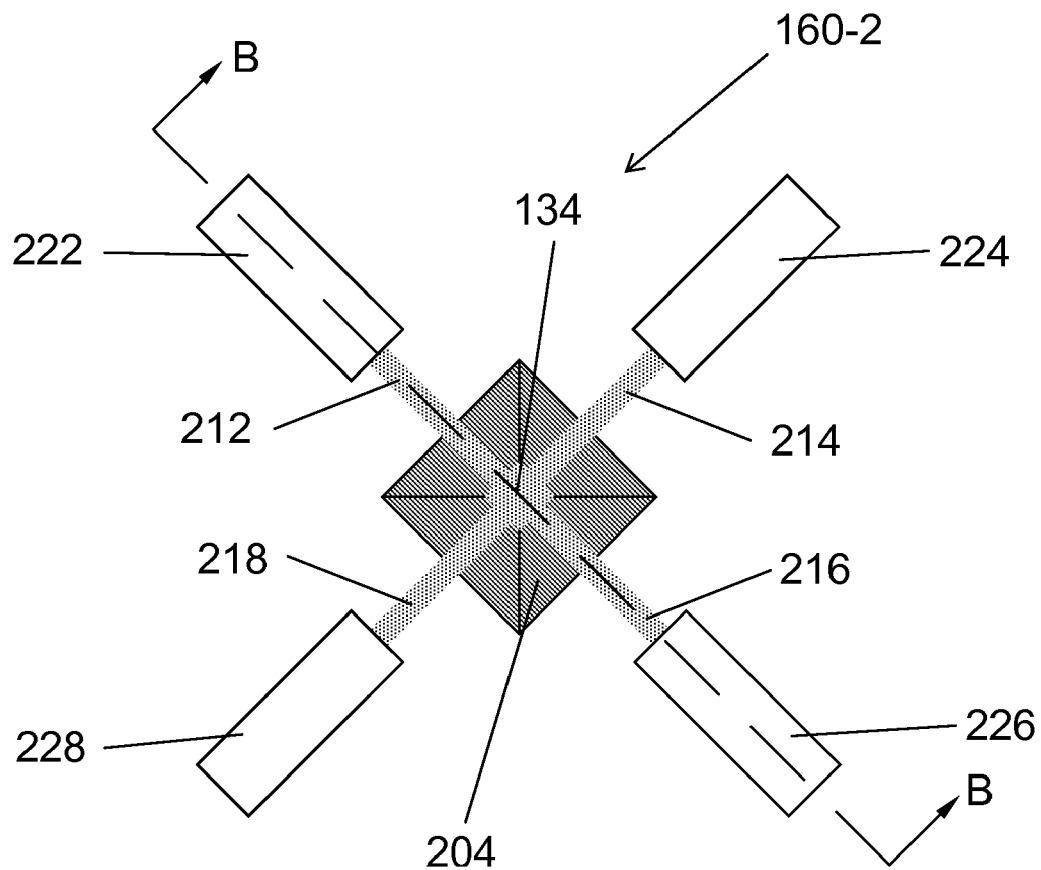
FIGS. 2A and 2B are schematic drawings that show a position-sensitive radiation detector system.
Figure 2B:
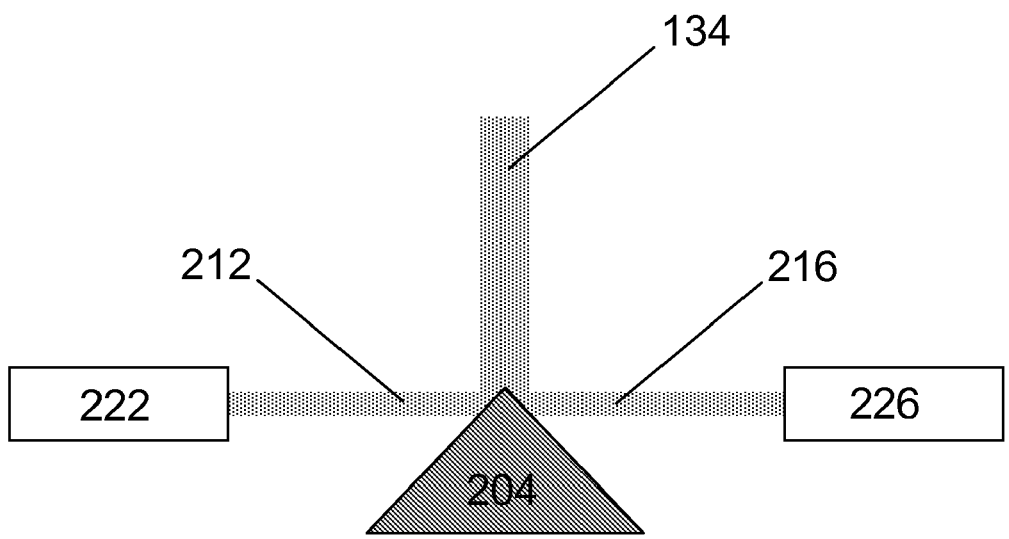
Figure 3B:
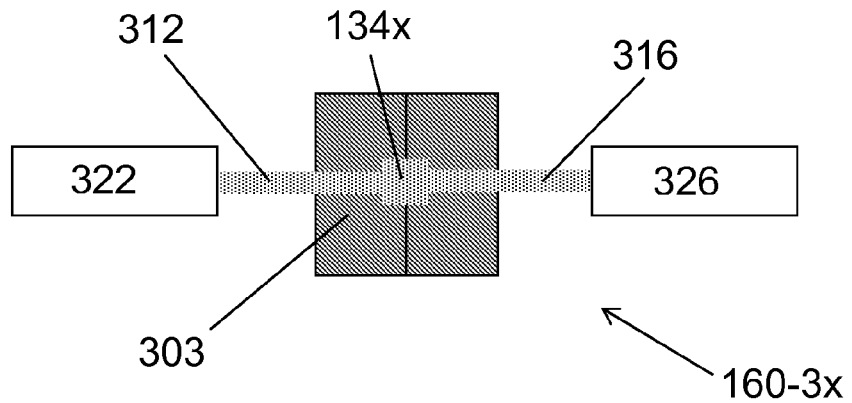
FIGS. 3A, 3B, and 3C are schematic drawings that each show a portion of another a position-sensitive radiation detector, according to an embodiment of the invention.
Figure 3A:
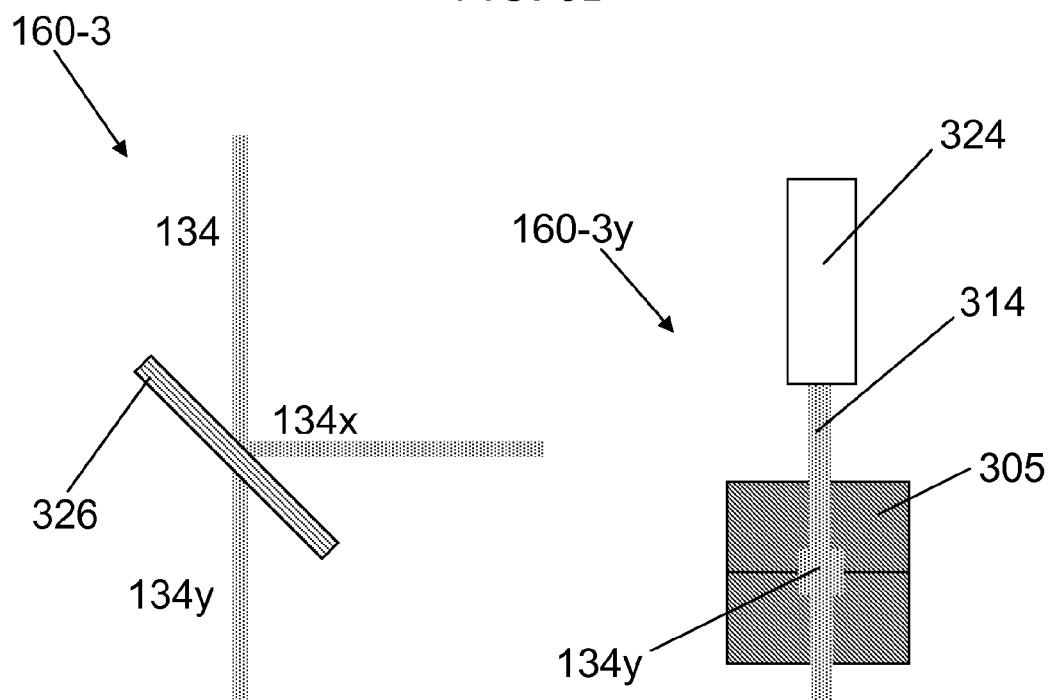
Figure 3C:
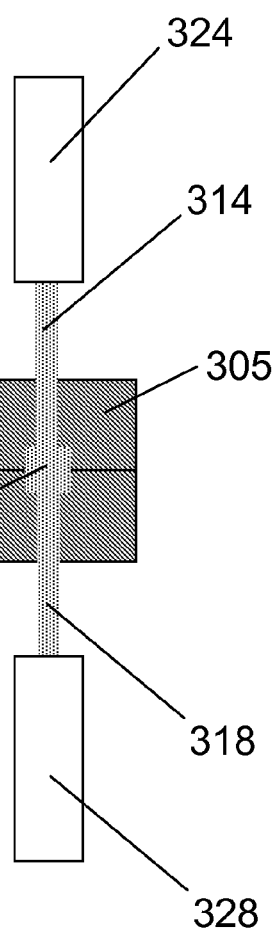
Figure 4:
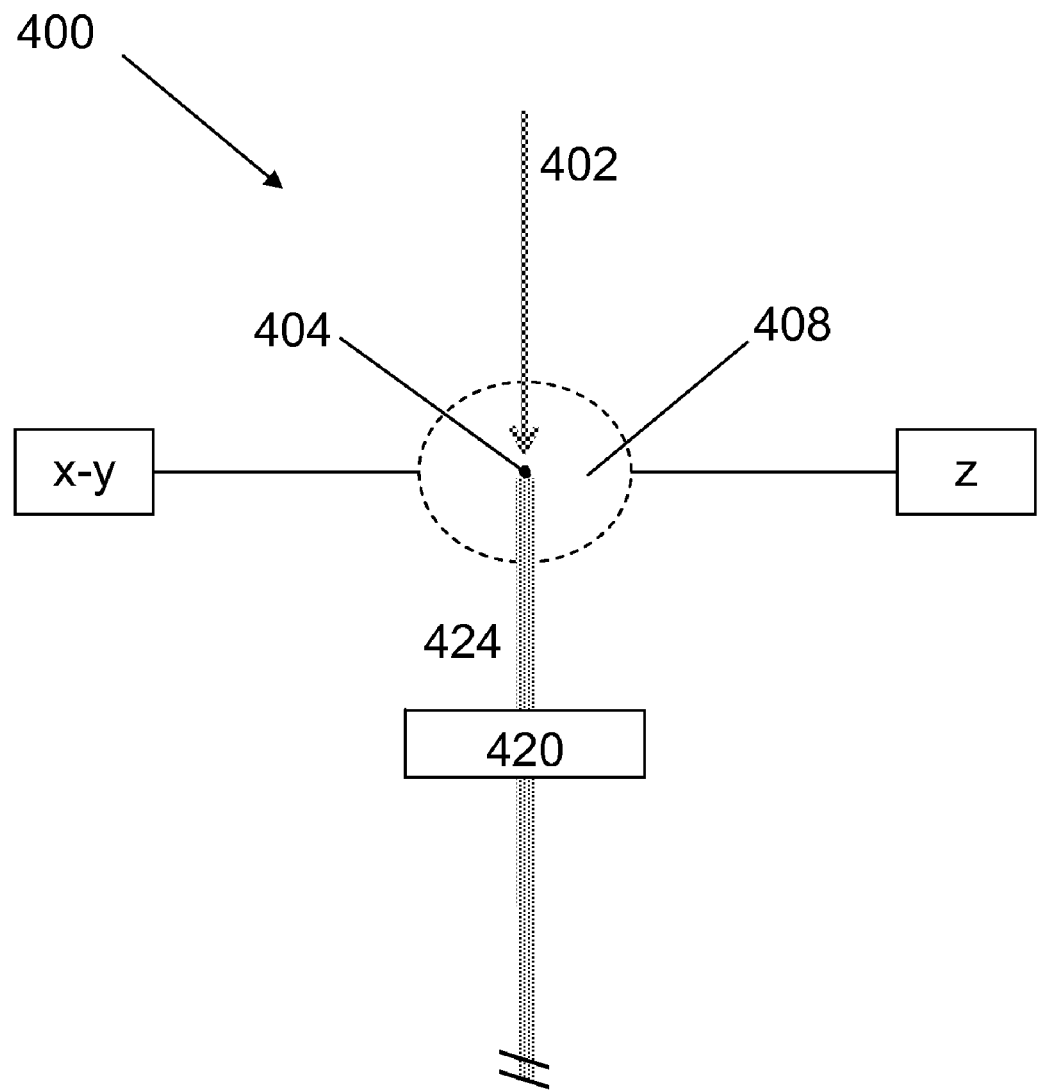
FIG. 4 is a schematic diagram of a portion of a system for non-invasively tracking a particle, according to an embodiment of the invention.
Figure 5:
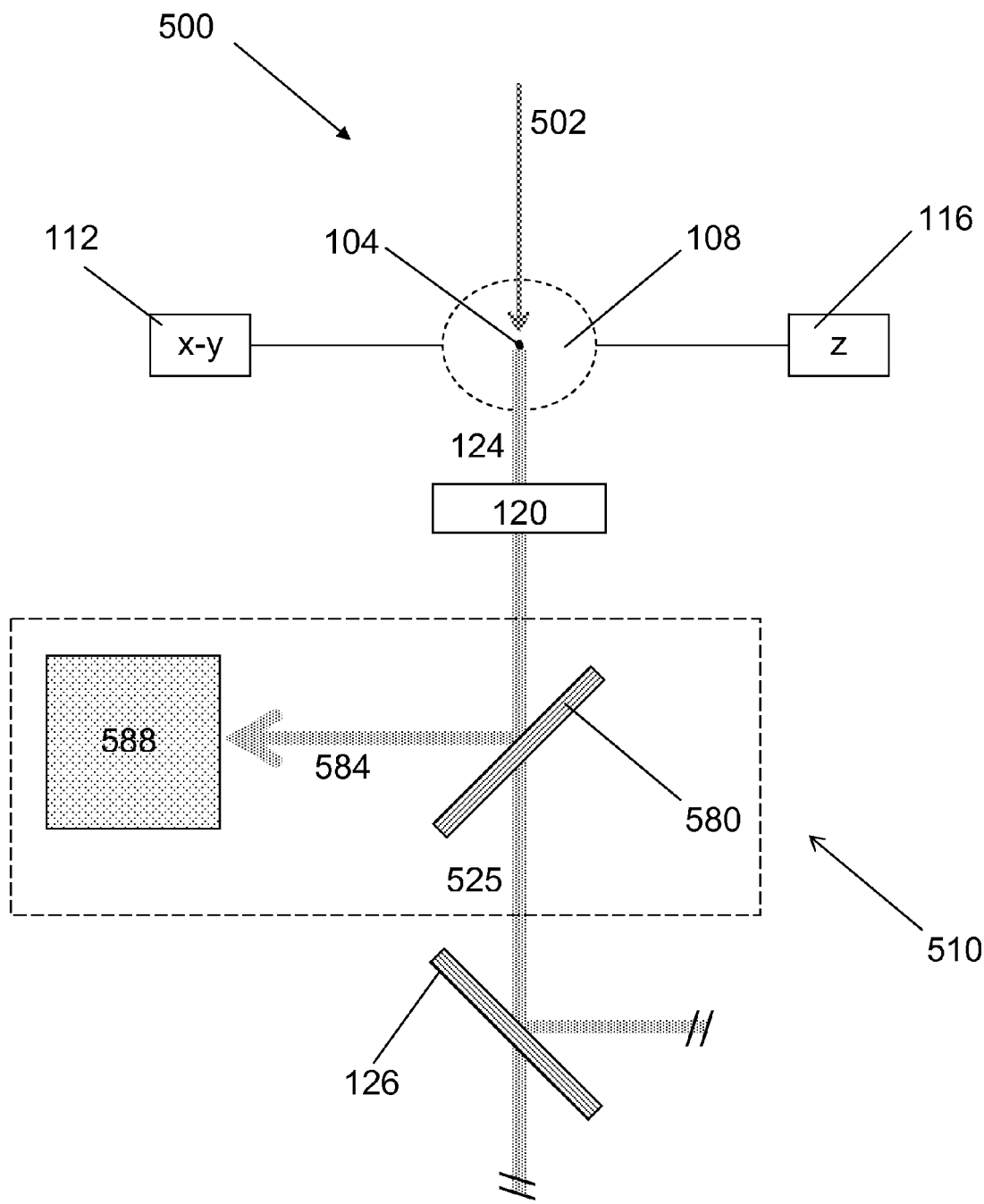
FIG. 5 is a schematic drawing that shows an additional module that can be added to a single particle tracking system.
Figure 6:
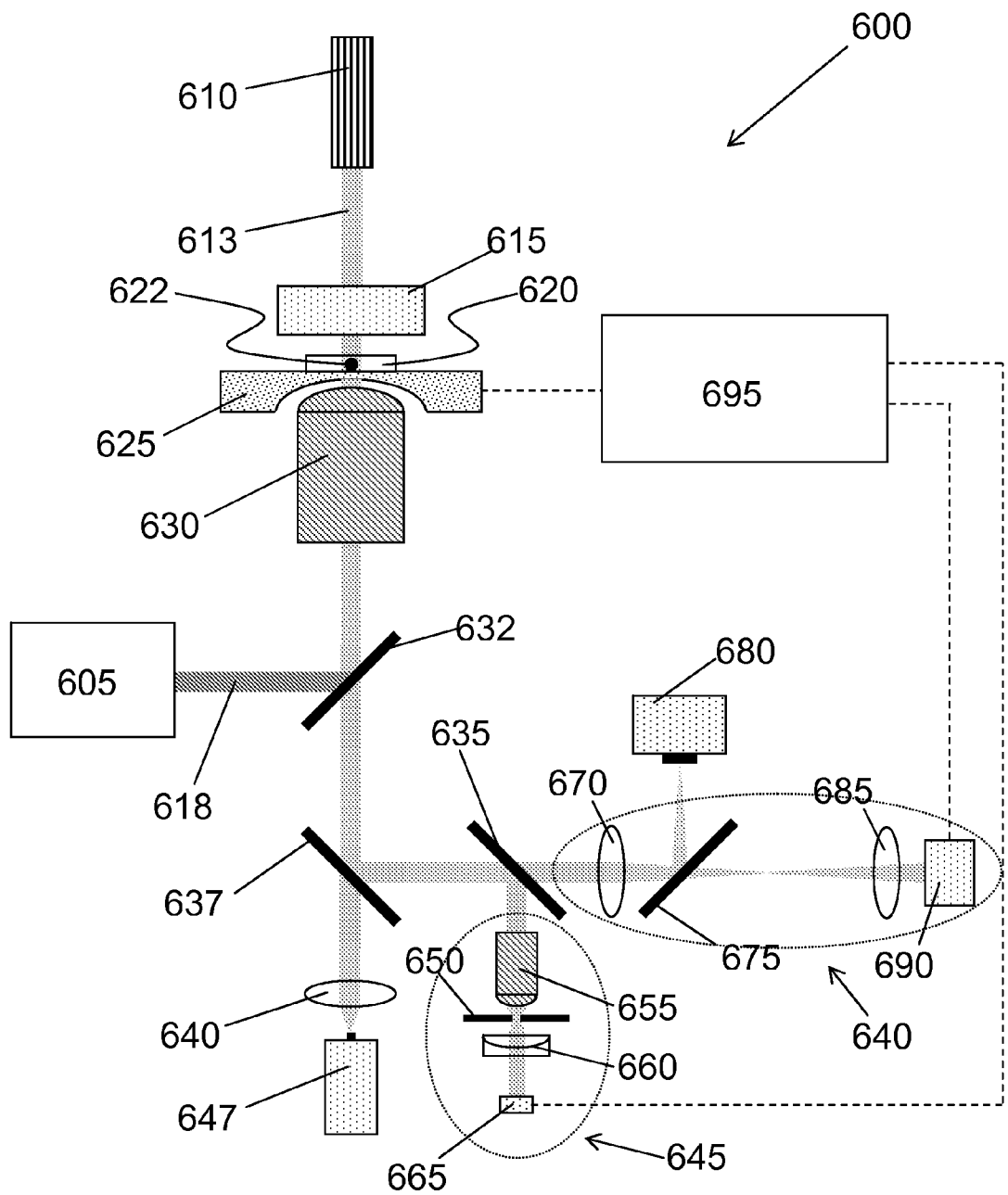
FIG. 6 is a schematic diagram that shows an exemplary system built around an inverted microscope, according to an embodiment of the invention.
Figure 7:
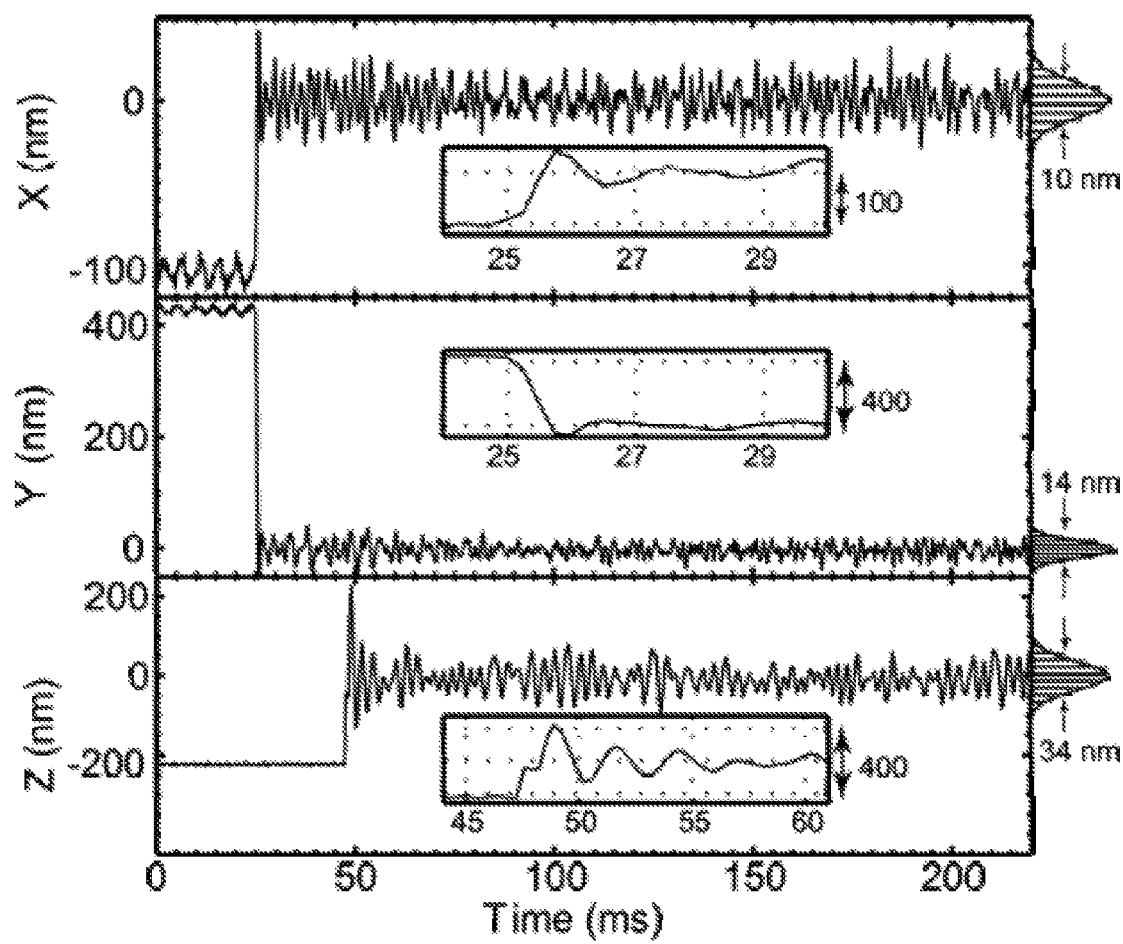
FIG. 7 is a plot of x, y, and z stage movements as a function of time.
Figure 8A:
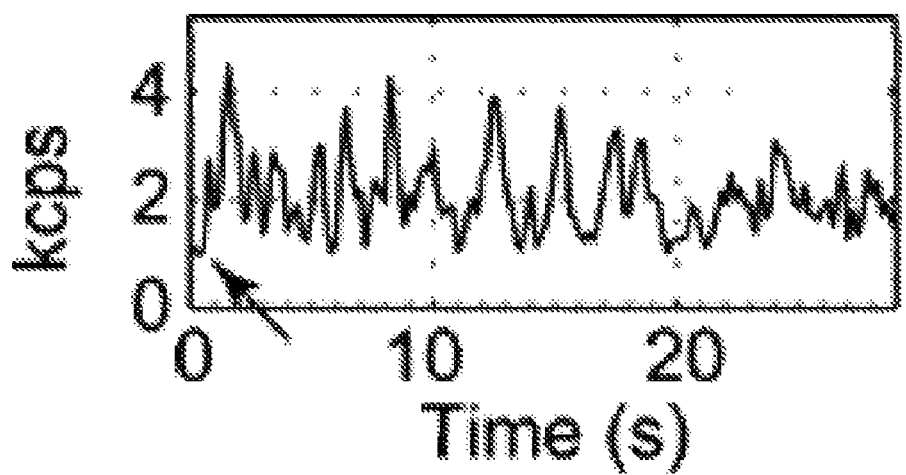
FIG. 8A is a plot of the intensity of back scattered green light as a function of time.
Figure 8B:
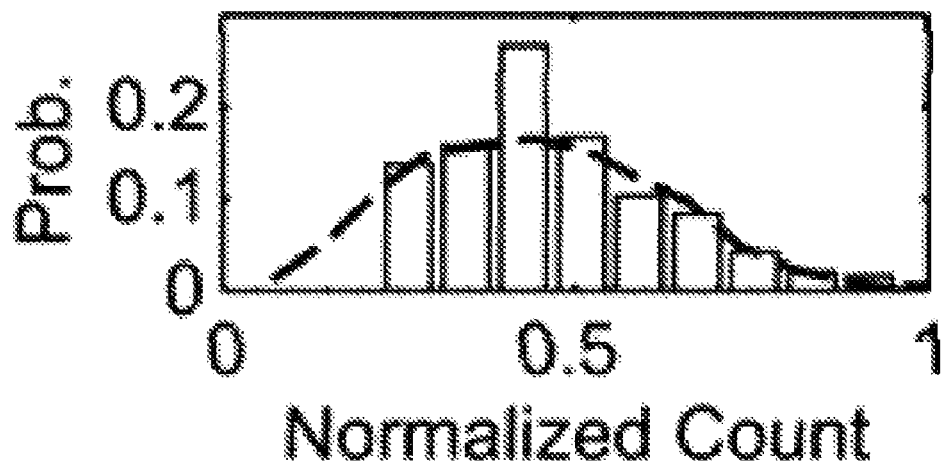
FIG. 8B is a plot of the mean square displacement of a gold nanoparticle as a function of time.
Figure 9A:
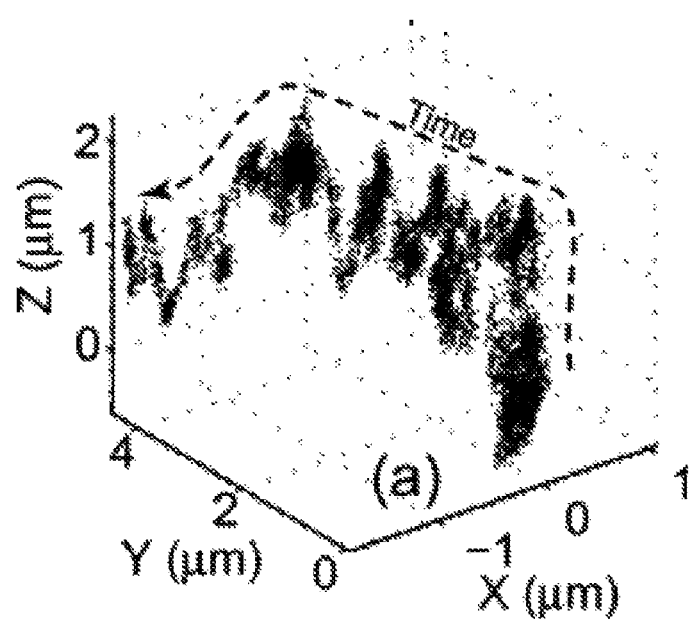
FIG. 9A shows the 3-dimensional trajectory of a 250-nm gold particle obtained by measuring the counter movement of the translation stage.
Figure 9B:
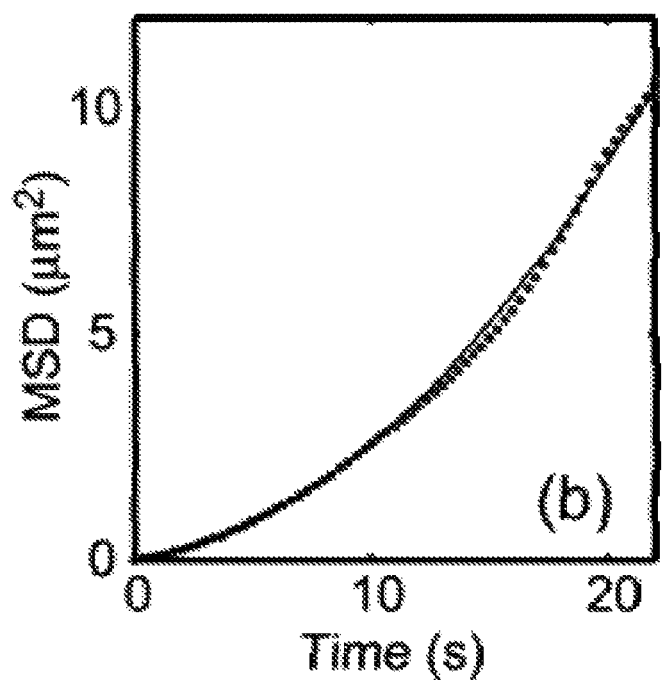
FIG. 9B shows a plot of the mean square displacement of the gold particle from the origin as a function of time. The dotted line in FIG. 9B is a plot of the mean square displacement of the gold particle from the origin as a function of time.

Tracking of individual nanoparticles has been achieved conventionally using video microscopy and laser scanning A limitation common to these two-dimensional techniques is that the particles are lost once they move out of the focal plane. Long-term recording of the precise 3D positions of a fast moving target smaller than the optical diffraction limit has posed significant challenges in noninvasive position sensing and feedback control until now. A single-particle three dimensional tracking system (3D-SPT) can record the motion of a particular nanoparticle and thus offers a solution to this problem and allows for spectroscopic and imaging studies at the single-particle level.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

We claim:

1. A system for non-invasively tracking a particle, comprising:
 a particle-holding device having an x-y position control and a z position control;
 a particle coupled to the particle-holding device;
 a first radiation-gathering component positioned to collect radiation from the particle;
 a beam splitter positioned to split the radiation collected by the first radiation-gathering component and to send the radiation along two distinct paths, a first path and a second path;
 a second radiation-gathering component within the first path to direct the radiation through an aperture and onto a single-element radiation detector;
 a first feedback control mechanism providing communication from the single-element detector to the z position control;
 a third radiation-gathering component within the second path to direct the radiation onto a position-sensitive radiation detector; and
 a second feedback control mechanism providing communication from the position-sensitive radiation detector to the x-y position control.

2. The system of claim 1 wherein the particle-holding device is selected from one or more of the group consisting of microscope stage, microfluidic devices, electrodes, magnetic fields, and electric fields.

3. The system of claim 1 wherein the x-y or z controls are of a type selected from the group consisting of piezoelectric devices, stepper motors, dielectrophoresis, microfluidic flow, and magnetic force manipulation.

4. The system of claim 1 wherein the radiation from the particle comprises scattered, refracted, phase-shifted, or emitted electromagnetic radiation or particle beams.

5. The system of claim 4 wherein the radiation from the particle comprises scattered electromagnetic radiation.

6. The system of claim 1 wherein the radiation-gathering components are selected from one or more of the group consisting of optical lenses and mirrors, x-ray lenses and mirrors, uv lenses and mirrors, infrared lenses and mirrors, microwave lenses and mirrors, gamma ray lenses and mirrors, and electromagnetic lenses and mirrors, as appropriate for the radiation collected.

7. The system of claim 1 wherein the aperture has an adjustable opening size.

8. The system of claim 1 wherein the radiation detectors can detect radiation of the type collected from the particle.

9. The system of claim 8 wherein the radiation detectors are selected from the group consisting of avalanche photodiodes, photon-counting avalanche photodiodes, scintillators, photomultiplier tubes, charge coupled devices, and Geiger counters.

10. The system of claim 8 wherein the position-sensitive radiation detector comprises a quadrant detector.

11. The system of claim 8 wherein the position-sensitive radiation detector is a unit comprising a radiation mirror having an acute angle and two single-element radiation detectors, one detector at each side of the radiation mirror, the detectors positioned to receive radiation reflected from a first set of opposite sides of the mirror.

12. The system of claim 11 wherein the mirror has a shape selected from the group consisting of triangular prism, square pyramid, tetrahedron and solid cone.

13. The system of claim 11, further comprising a second unit positioned 90° from the first unit.

14. The system of claim 11 wherein the mirror is square pyramidal or conical and further comprising two addition single-element radiation detectors positioned to receive radiation reflected from a second set of opposite sides of the mirror, the second set orthogonal to the first set.

15. The system of claim 1 wherein the feedback control mechanisms are selected from the group consisting of analog circuits, digital signal processes, field programmable gated arrays, and software running on a computer or micro-controller.

16. The system of claim 1, further comprising a source of radiation directed onto the particle.

17. The system of claim 16 wherein the source of radiation is an infrared laser.

18. The system of claim 1, further comprising an apparatus to record movement of the particle-holding device.

19. The system of claim 1, further comprising a spectroscopy unit configured to collect spectroscopic information from the particle.

20. The system of claim 1, further comprising an imaging unit configured to make an image of the particle.

21. A system for non-invasively tracking a particle, comprising:
    a stage having an x-y position control and a z position control;
    a particle coupled to the stage;
    a first lens positioned to collect light from the particle;
    a beam splitter positioned to split the light collected by the first lens and to send the light along two distinct paths, a first path and a second path;
    a second lens within the first path to direct the light through a pinhole and onto a single-element APD;
    a first feedback control mechanism providing communication from the single-element APD to the z position control;
    a third lens within the second path to direct the light onto a position-sensitive light detector; and
    a second feedback control mechanism providing communication from the position-sensitive light detector to the x-y position control.

22. A method of tracking a particle, comprising the steps of:
    providing a particle coupled to a particle-holding device, the device having an x-y position control and a z position control;
    collecting radiation from the particle with a first radiation-gathering component;
    splitting the radiation and sending the radiation along a first path and a second path;
    directing the radiation in the first path through an aperture and onto a single-element radiation detector;
    providing communication from the single-element detector to the z position control;
    directing the radiation in the second path onto a position-sensitive radiation detector; and
    providing communication from the position-sensitive detector to the x-y position control.

* * * * *